United States Patent

Sandoz

[11] Patent Number: 5,567,871
[45] Date of Patent: Oct. 22, 1996

[54] PROCEDURE AND APPARATUS FOR CHECKING THE STATE OF DEGRADATION OF WOODEN STRUCTURES, ESPECIALLY POLES

[76] Inventor: Jean-Luc Sandoz, 23 avenue de la Gare, 1022 Chavannes Sur Renens - Suisse, France

[21] Appl. No.: 416,620

[22] Filed: Apr. 5, 1995

[51] Int. Cl.⁶ .................................................. G01N 3/00
[52] U.S. Cl. .................................................. 73/85; 73/81
[58] Field of Search ........................... 73/788, 78, 81, 73/83, 84, 85

[56] References Cited

U.S. PATENT DOCUMENTS

| | | |
|---|---|---|
| 2,389,030 | 11/1945 | Dana . |
| 4,249,414 | 2/1981 | Barth . |
| 4,283,939 | 8/1981 | Edward, Jr. ........................... 73/81 |
| 4,343,179 | 8/1982 | Astrom et al. . |
| 4,492,111 | 1/1985 | Kirkland ............................... 73/84 |

FOREIGN PATENT DOCUMENTS

| | | |
|---|---|---|
| 2638261 | 3/1977 | Germany ............................... 73/81 |
| 2919541 | 12/1979 | Germany . |
| 1769075 | 10/1992 | Russian Federation ............... 73/81 |

*Primary Examiner*—Richard Chilcot
*Assistant Examiner*—Max Noori
*Attorney, Agent, or Firm*—Harris Beach & Wilcox, LLP

[57] ABSTRACT

The strength of an upright wooden structure is diagnosed by drawing a pair of spaced apart electrodes into the structure to a predetermined depth. The force of penetration and the moisture content of the structure at the depth of penetration are measured and the measurement data processed to provide an instantaneous readout indicative of the strength of the structure.

8 Claims, 3 Drawing Sheets

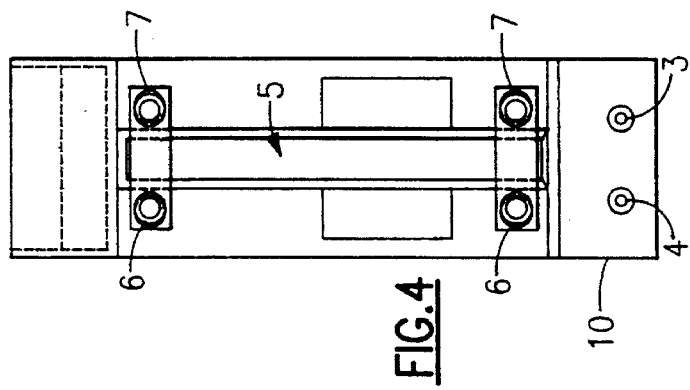
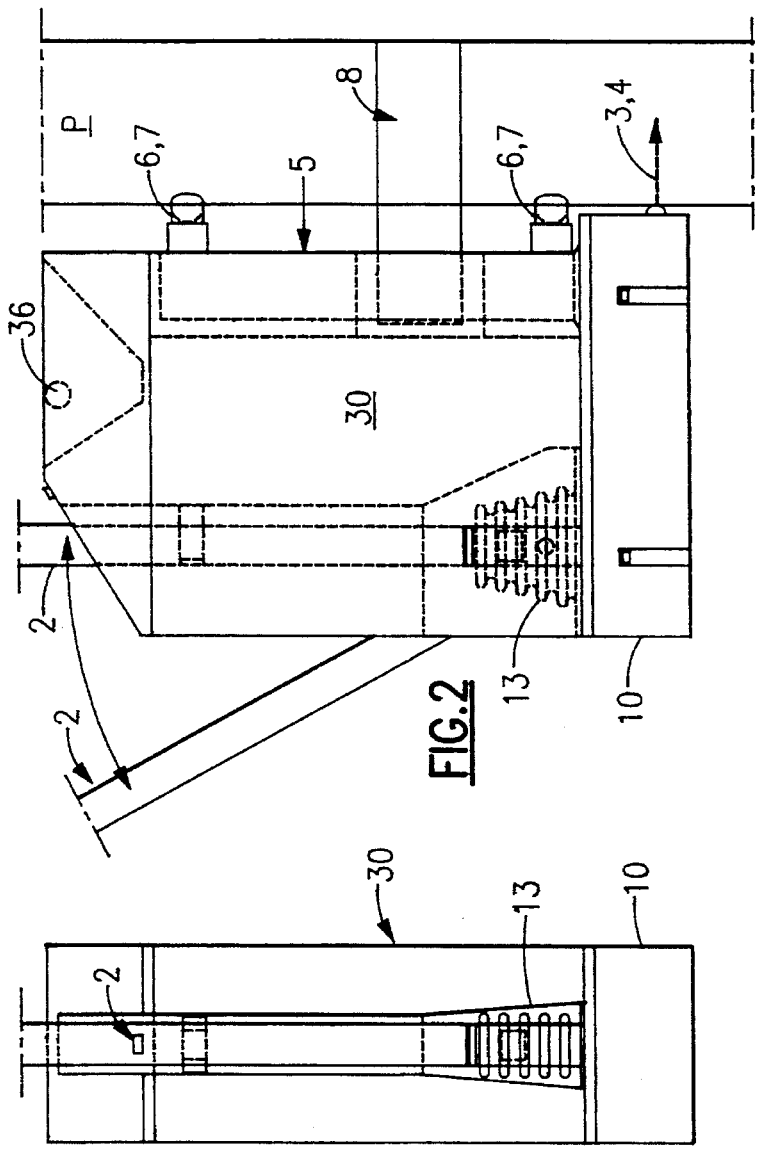
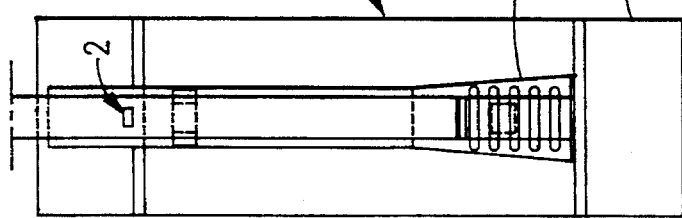
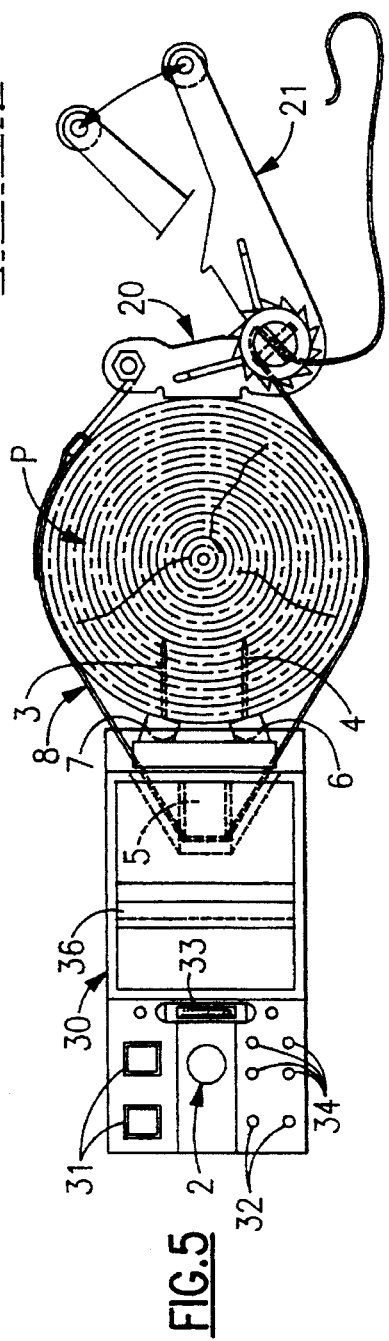

PROCEDURE AND APPARATUS FOR CHECKING THE STATE OF DEGRADATION OF WOODEN STRUCTURES, ESPECIALLY POLES

BACKGROUND OF THE INVENTION

The present invention relates to a procedure, and an apparatus for the implementation of said procedure, making it possible simply, effectively and rapidly, to check the physical state of trees, of wood and of wooden structures, and more particularly of poles (telephone poles, electrical poles, etc.), incorporating density variations, and, over time, exposed to the risk of biological degradation diminishing their initial properties.

There are, for example, millions of wooden poles in use in the world (10 million in France and 200 million in the United States, for example) which have to be periodically checked in order to maintain the lines, such as, for example, telephone and power lines, the main difference between these applications residing in the diameter of the poles which is smaller for telephone lines (of the order of 17 to 20 cm) than that of power lines (which is of the order of 20 to 40 cm).

One of the main problems which arises with such elements is that of periodically checking them, in order to verify their condition, so as to decide on maintenance and/or replacement operations, should this be necessary, for example if they present a risk of breaking, this being unacceptable given the fact that, at least as regards telephone poles, the personnel very often work by directly scaling the pole and that, every year, accidents happen, sometimes fatal accidents, because of the mechanical fragility of some of the supports.

Currently, the solution still commonly used to carry out such a check very often employs an empirical method based on the human ear, the checker giving the pole a few blows with a hammer and, depending on the acoustic response of the wood, determining a diagnosis on the state of the pole by virtue of his personal experience.

To date, many proposals have been made for carrying out such a check by means of a measurement apparatus, as emerges especially from U.S. Pat. Nos. 2,389,030, 4,343, 179 and 4,249,414.

In general, the proposed solutions according to these documents consist in carrying out a local hardness measurement. In the case of the first document, the resistance to screwing a metal auger into the wood is measured, in the second, a "spike" is forced in linearly by a dynamometric system and finally, in the last case, the local hardness of the outer zone is measured so as to determine whether the pole exhibits the characteristics of being hard at the surface, and consequently of preventing the anchoring of a technician's grapplers for climbing, by means of a measurement assembly which penetrates slantwise into the perimeter, making an angle of a few degrees, with respect to the surface of the latter.

Such hardness measurements lack accuracy and reproducibility because they do not exclude penetration by the element into a crack due to drying-out of the pole. Moreover, they are dependent on a constant force which therefore leads to a variable penetration and to a diagnosis which is therefore never made with the same geographic coordinates.

In addition, the solutions described in these documents are very sensitive to diameter variations, the penetration of the auger or of the spike not always being made along the diametral axis, which leads to a measurement away from the natural radial axis of the wood and therefore constitutes an additional inaccuracy.

Finally, all the apparatuses proposed to date take into account just one factor enabling the residual strength of the wood to be checked, namely its hardness, and do not take into account a factor which is that of moisture content which can cause damage due to rotting of the pole and can weaken it at its center without giving any indication of weakness on the outside. In fact, since the poles are treated in an autoclave, the outer layer, which may go from 2 cm for spruce to 5 cm for pine, is more resistant over time. A single hardness measurement does not make it possible to detect whether damage is occurring, through the heart of the pole, and the weakening at its center, for example as a result of rotting.

SUMMARY OF THE INVENTION

It has also been proposed, as emerges especially from DE-A-2,919,541, to carry out the measurement of moisture in a hygroscopic material, and more particularly wood, by means of penetrating electrodes which are fixed to the head of a mallet enabling them to be put into position and/or which are positioned on the head of a hammer which, by virtue of its mass also enables these electrodes to be made to penetrate into the material to be measured.

The object of such a measurement is to determine the exact value of the moisture content of the wood and therefore such a measurement does not make it possible to give an indication, on the basis of various predetermined thresholds above which the moisture level is capable of causing the formation of active fungi, leading to a risk of internal degradation of the wood, or, on the other hand, if the amount measured is below a critical threshold, of being able to ensure that there is no risk of biological activity and that the wood is therefore sound.

An improved procedure together with an apparatus enabling it to be implemented has been found, and it is this which forms the subject of the present invention, which makes it possible, easily and reliably, to establish a diagnosis of the state of wood, poles or similar structures. Moreover, the procedure in accordance with the invention allows optimization of the intervention operations and of the timescales for changing, by making it possible to accumulate reliable and accurate statistical data about the physical and mechanical state of the poles or other wooden structures.

In general, the procedure in accordance with the invention making it possible to establish a diagnosis of the state of trees, of wood and of wooden structures, and more particularly of poles or similar structures, so as to determine the mechanical characteristics of them and therefore their strength, with a view to making a selection of living trees or to identifying weakened or dangerous poles to be climbed in order to provide upkeep and maintenance on them, consists in carrying out a measurement of the hardness of the wooden structure by depthwise penetration into its thickness of a measurement element, wherein:

the hardness measurement element is constituted by an assembly comprising two spikes which are simultaneously actuated and penetrate by means of pressure into the structure on either side of a rigid measurement spacing, and over a predetermined and constant depth, the actual penetration force being measured by a force sensor;

simultaneously with this hardness measurement, a measurement of the moisture content of the wood at a constant depth is performed, enabling the risk of internal biological damage to be evaluated;

the information obtained being processed in order to give an instantaneous result relating to the strength of the structure.

Preferably, in accordance with the procedure according to the invention, the measurement of the hardness of the wood and of the moisture content are carried out as close as possible to ground level, the spikes which enable the local hardness to be measured being insulated over their length and constituting electrodes making it possible to check the moisture according to the resistive method, the resistivity of wood being inversely proportional to the water content.

The invention also relates to an apparatus which enables the aforementioned procedure to be implemented and which, in addition to its simplicity, makes it possible to carry out very accurate measurements and to establish a reliable diagnosis, this being so on wooden elements which may be of variable diameters.

In general, such an apparatus comprises:

an all-welded longitudinal body incorporating two pairs of positioning stops enabling the apparatus to be mounted along the longitudinal generatrix of the wooden structure, such as a pole, fixing being achieved by means of at least one strap that is positioned around the structure, and the two ends of which comprise joining and locking means;

a case fixed to the base of the longitudinal body and comprising the measurement and application members constituted by an assembly comprising two spikes associated with a force sensor and driven translationally by means of an operating arm, said spikes constituting electrodes enabling the depthwise moisture content of the wooden structure to be measured;

the whole assembly being managed by processing software making it possible to give an instantaneous result concerning the strength of the pole.

According to a preferred embodiment enabling the two spikes to penetrate simultaneously into the wooden structure on either side of a rigid measurement spacing, over a predetermined depth, the position of the apparatus against the structure is achieved by means of four supports constituted by two pairs of stops arranged symmetrically on either side of the midplane between the two planes of penetration by the measurement spikes into the wood, the support stops being positioned in the region of these penetration generatrices. Such a structure enables a very accurate measurement to be obtained.

In the rest of the description, the invention will be described more particularly for the checking of wooden poles, it being understood that this is not limiting and that, as indicated in the preamble, the procedure and the apparatus for its implementation may be used not only to check structures other than poles, such as beams, trusses, etc., but also to determine the characteristics of a living tree, thus enabling a selection by density to be made.

BRIEF DESCRIPTION OF THE DRAWINGS

The manner in which the invention is implemented will, however, be better understood by virtue of the following illustrative embodiment which is given by way of indication, but in no way implying limitation, and which is illustrated by the appended diagrams in which:

FIGS. 2, 3, 4 and 5 are respectively views in elevation, end on and from above, of a specific embodiment of an apparatus in accordance with the invention, the elevation view (FIG. 2) and the view from above (FIG. 5) showing precisely how it is positioned against the surface of the pole to be checked;

DESCRIPTION OF THE INVENTION

Figure 1:
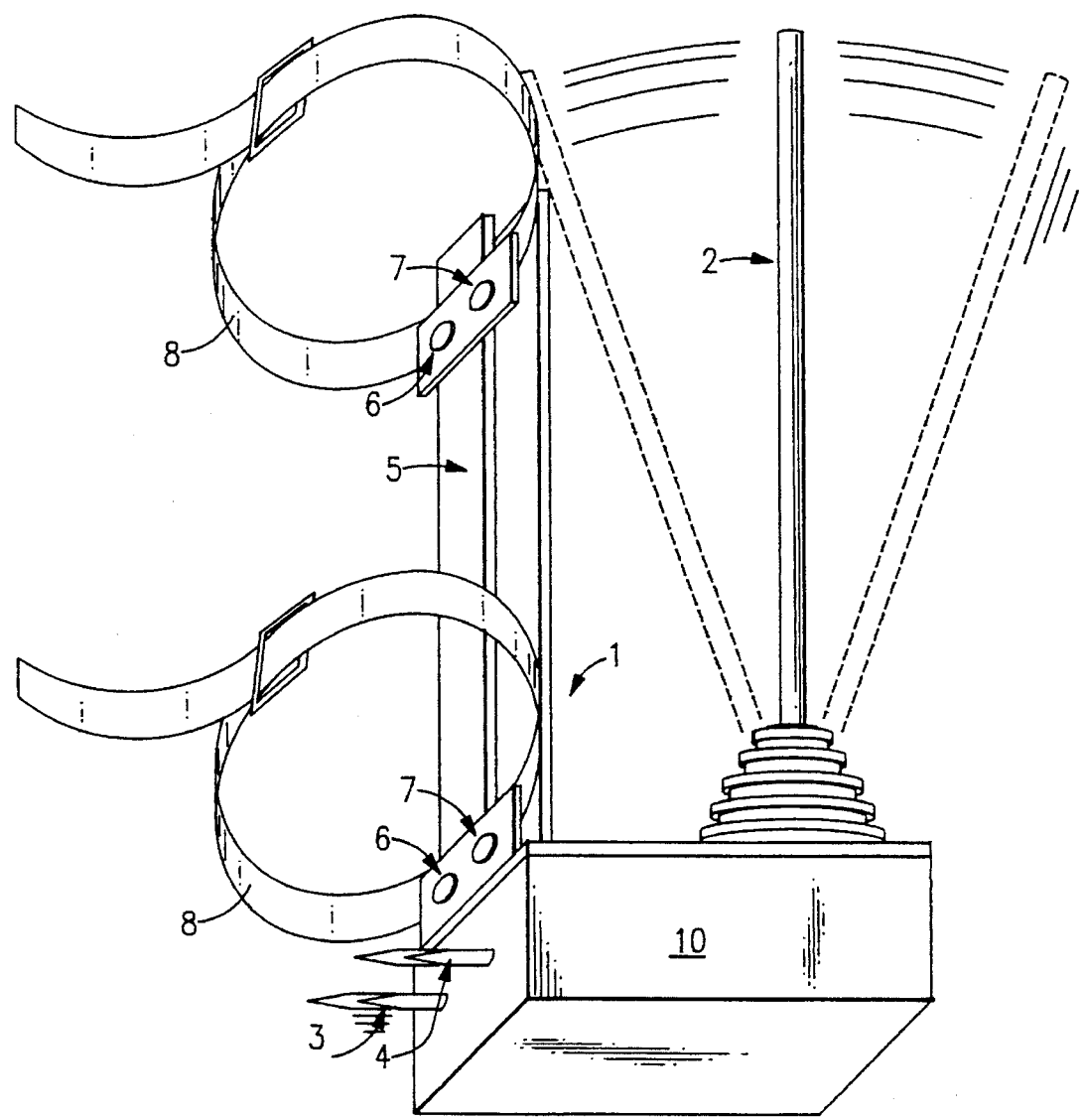
FIG. 1 is a perspective diagrammatic view showing the general structure of an apparatus enabling the procedure in accordance with the invention to be implemented.

In general, the procedure in accordance with the invention, making it possible to establish a diagnosis of the physical state of wood or of wooden structures, more particularly of poles, so as to determine their possible level of degradation, consists in carrying out, by means of a portable measuring apparatus, such as shown diagrammatically in FIG. 1, on the one hand a measurement of the hardness of the wooden structure by depthwise penetration into its thickness of a measurement element, but also and simultaneously a measurement, also depthwise, of the moisture content of the wood, as close as possible to ground level. The measurement of these variables makes it possible, by means of calibrated processing software, to give an instantaneous and accurate result to the user, for example in the form of colored lights, a green light indicating that the structure is good whereas a red light will indicate, on the contrary, that the structure is dangerous, or in digital form which can be transferred to a microcomputer for maintenance statistics, confirming whether the pole is in good condition and therefore may be climbed by a technician without danger, or whether, on the contrary, it has to be visited again within a short space of time, or indeed even changed.

The depthwise hardness measurement is, in accordance with the procedure according to the invention, carried out by simultaneous penetration by two spikes which penetrate by means of pressure into the structure on either side of a rigid measurement spacing, over a predetermined and constant depth, the actual penetration force of the two measurement members being measured by a force sensor.

In order to carry out the measurement of the depthwise moisture content in the wood, various techniques may be envisaged such as those making use of the insulating properties of anhydrous wood (unstable state) and of the conducting properties of wood containing moisture. These techniques are called "resistive" techniques, the resistivity of wood being inversely proportional to its water content. This measurement technique is advantageously used for the implementation of the invention, since it makes it possible to perform a depthwise measurement of the moisture content, for example at 40 mm from the surface, by virtue of electrodes which are insulated over their length and which, advantageously are constituted by the same spikes which enable the resistance to penetration into the wood to be measured.

Possibly, other known methods for measuring the moisture content, for example capacitive methods measuring the phase shift of a high-frequency wave after propagation in the material, could be envisaged. Such methods, which may be more accurate, are, however, more tricky to implement as a result of the surface state and coupling state, the sensitivity to the fibre angles, to the varieties of wood, etc.

The appended figures illustrate a preferred embodiment of an apparatus enabling the procedure in accordance with the invention to be implemented, which apparatus makes it possible simultaneously to take the measurement of local hardness in the region of ground level and the measurement of the moisture content, by means of an assembly comprising two simultaneously actuated spikes which are associated with a force sensor and controlled translationally by means of an operating arm, said spikes constituting the electrodes which enable the depthwise moisture content of the wooden structure to be measured.

Such an apparatus is essentially composed of an assembly designated by the general reference (1) essentially comprising an all-welded longitudinal body (5) to which two pairs of positioning stops (6, 7) are fitted, these being arranged on either side of the vertical plane of symmetry of said body and intended to bear against the structure to be checked on either side of a rigid measurement spacing. These two pairs of stops (6, 7) are separated from each other by a distance of the order of a few tens of centimeters, so as to guarantee that the apparatus fits precisely along the longitudinal generatrix of the pole, the base of the apparatus being arranged in the vicinity of the ground level. This body (5) is fixed to the pole by means of at least one strap. In the example shown diagrammatically in FIG. 1, two straps (8) are provided in the region of the positioning stops; however, in the embodiment illustrated in FIGS. 2 to 6, a single strap (8) arranged in the intermediate zone between the pairs of stops (6, 7) and surrounding the column (5) turns out to be enough. The ends of this strap comprise means making it possible to lock the apparatus against the pole (P), constituted, for example, by a system (20) based on toothed clicks and ratchets actuated by a lever (21).

Figure 7:
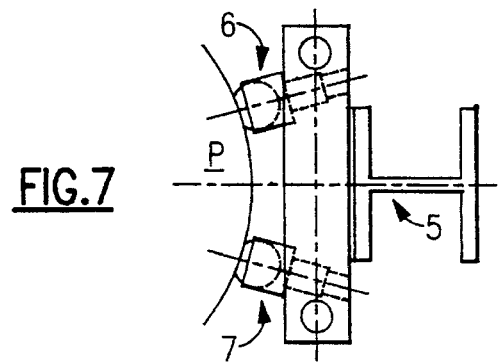
FIG. 7 is a view from above, in section along the axis I—I of FIG. 6, showing in detail the manner in which the apparatus in accordance with the invention is held positioned against the surface of the pole to be checked.

The presence of four supports (6, 7) makes it possible to ensure perfect fitting against the surface of the structure to be checked. As is clearly apparent from FIG. 5 and FIG. 7, these supports (6, 7) are oriented so as to converge towards the rigid measurement spacing. Moreover, as is apparent from FIGS. 4 and 5, these supports (6, 7) are arranged in the region of the plane of penetration of the spikes/electrodes (3, 4) performing the hardness and moisture-content measurement. Finally, these supports (6, 7) are themselves synchronized onto a reference-position detector when the head of the electrodes is in contact with the surface of the longitudinal generatrix of the wood.

Figure 6:
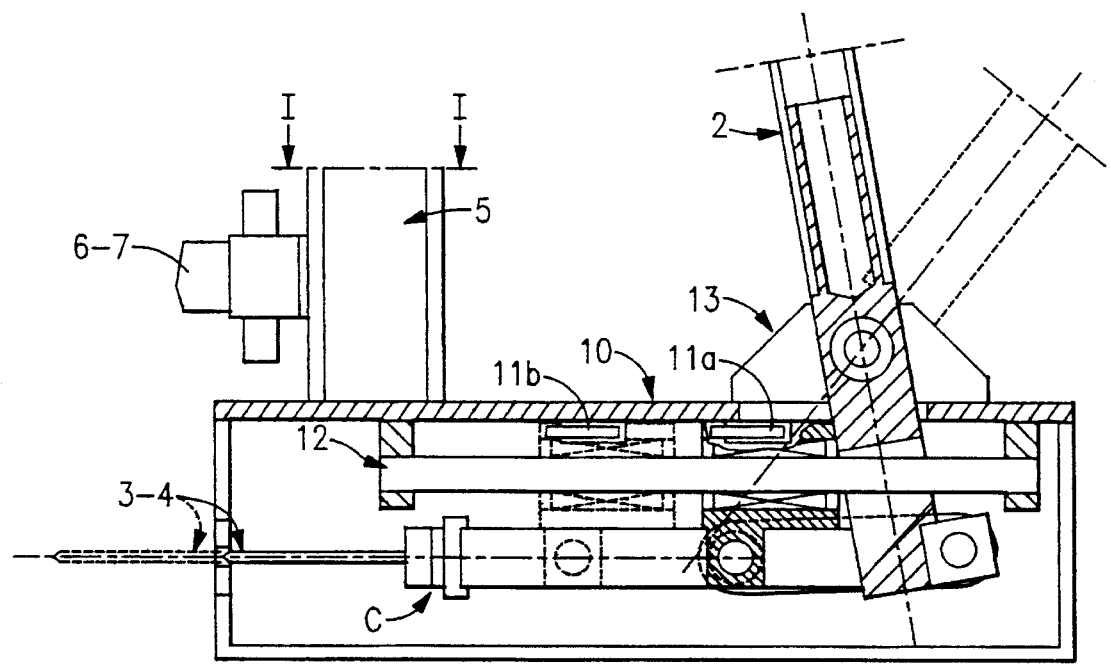
FIG. 6 is a partial detailed view, in elevation and in section, showing the structure of the means which an apparatus in accordance with the invention comprises in order to ensure penetration by the measurement means into the pole to be checked.

Associated with this all-welded longitudinal body (5) is a case (10) containing the measurement and operating members, that is to say essentially the electrodes (3, 4), the force sensor (C), the translation device, the structure of which is more particularly apparent in FIG. 6 and which is controlled by an operating arm (2). Advantageously mounted on top of the case (10) is a cover (30) on which are arranged the buttons (31) for starting and stopping the apparatus, the display of the data on colored lights (32) as well as the link (33) to a microcomputer. Arranged inside the base and the cover are the means which make it possible to provide the memory for the management of the measurement cycle and the data-acquisition storage.

Also arranged inside the case (see FIG. 6) are start-of-travel and end-of-travel sensors (11a, 11b), an electrical power supply and a measurement chain for the force sensor (C) and for the resistivity between the electrodes (3, 4). A set of lights (34) (see FIG. 5) makes it possible to display, in a color code, the physical or mechanical state of the pole. A handle (36) is provided on top of the cover in order to enable the apparatus to be easily transported from one site to another.

The penetration by the spikes of the electrodes (3, 4) into the pole (P) is achieved by the manual force of the user acting on the operating arm (2), the depth of penetration, which depends on the length of the spike/electrode, possibly being variable but generally being calibrated to 40 mm. By way of indication, the maximum forces necessary for penetration of the spikes (3, 4) into a new pole of high density are approximately 3000N per pair of electrodes of 3 to 3.5 mm in diameter. This force corresponds to the pressure peak observed after 40 mm of penetration, taking into account not only the pressure but also the frictional forces. The maximum penetration of the electrodes is depicted by the dotted lines in FIG. 6.

In order to guarantee engagement and disengagement of the electrodes, they are moved by a linear translation of the means for supporting the electrodes, this also being the means for supporting the force sensor. This translation is brought about by human action and it is guaranteed in the mechanical guiding system (12) which is protected by the case (10) and sealed by a bellows (13), which guiding guarantees constant translation over time, especially as regards frictional forces. This also contributes to the accuracy and reliability of the performance of the apparatus.

The measurement pressure is not influenced by the diameter of the pole by virtue of the provision of a system of positioners aligned on the electrodes. As a consequence, by virtue of the invention, it is possible to check poles of different diameters (from small-diameter telephone poles to poles for medium- to high-voltage power lines). The force sensor shown behind the head of the electrodes measures the force of penetration by said electrodes with an accuracy greater than 2%. The quality of the translation makes it possible to have excellent repeatability of the measurements.

The body of the case (10) of said apparatus incorporates the wiring for the pair of measurement members (3, 4) so as to connect them to the management unit. The management is carried out in real time, with transmission of the information, for example to lamps, indicating the instantaneous state of the wood or of the pole, or else by linking to a microcomputer capable of interpreting the actual measurements taken, it being possible for these to be stored in the apparatus, for statistical studies aiming to optimize the maintenance of the plant visited. It could be envisaged to use other means of processing, for example before storage or by means of serial-line outputs.

When the electrodes (3, 4) are at the end of their travel (after 40 mm of penetration, for example), the sensor transmits the information and initiates the collecting of the measurements of the hardness by reading the force sensor.

As regards the moisture content, this is measured in the head of the electrodes (3, 4), this making it possible to know the depthwise moisture content of the pole. The body of the electrodes is insulated so as not to be disturbed by the surface moisture content.

The measurement of the moisture content is carried out very accurately on account of the fact that it is performed with the electrodes acting in a horizontal plane in the pole embedded in the ground, this therefore guaranteeing a measurement through a greater layer of cells.

Such an apparatus has a simple design and is easy to operate, the movements of the electrodes (3, 4) being easily accomplished by means of the movements of the lever arm (2) about its pivot point; the travel of the electrodes is limited by a small check chain or by other equivalent means.

It should also be noted that the way in which the apparatus in accordance with the invention is fixed makes it possible to achieve very great stability in the fixing to the pole by virtue of the presence of four constant supports, these being reproducible whatever the diameter of the pole and being stable whatever its hardness, the measurement elements penetrating, for example, precisely along the diametral axis.

Compared to the prior solutions, such a procedure and apparatus has many advantages and leads to very accurate measurement, on account of the fact that it is based on the metrology of two variables, namely the local hardness and the moisture content. The fact that this measurement is performed by means of two spikes eliminates any risk of a false measurement, for example by penetration into a crack in the pole, the procedure according to the invention, making it possible to measure a force using a force sensor, and this being done at a constant distance (that of the penetration of all the spikes), guarantees accuracy in the hardness measurement. Moreover, the depthwise measurement of the moisture content makes it possible to determine whether the structure has not been weakened by the biological action of a lignivorous fungus, this measurement making it possible to demonstrate a moisture-content range corresponding to the possibility of the presence of the parasite. The purpose of this measurement is not to give a strictly accurate value of the moisture content but only an indication of a biological nature, namely whether the wood probably contains an active fungus or whether it is sound.

Finally, according to the invention, the processing of the results is based on electronic analysis and a diagnosis is made on the basis of a laboratory calibration, providing a characteristic strength of the pole for each pair of measured data. The interpretation performed by the machine transposes signals to the user by means of light-emitting diodes indicating different states, for example a very good state, a good state, one in the course of weakening and weakened, and one which is very much weakened and dangerous.

Such a type of diagnosis therefore guarantees the operating safety of the network as well as better management of the maintenance of the plant visited, by the processing via a microcomputer of all the actual data measured and stored temporarily in the apparatus.

Of course, the invention is not limited to the embodiment described above, but encompasses all alternative forms of it which are made in the same spirit.

I claim:

1. A process for diagnosing the state of an upraised wooden structure such as a pole having a treated outer layer to determine the mechanical characteristics of the structure that includes the steps of driving tips of a pair of parallel spaced apart measurement electrodes perpendicularly to a depth of at least approximately 40 mm into an upraised wooden structure to measure the condition of the structure beyond the treated outer layer, measuring the penetration force required to drive each element to said first depth, connecting said electrodes to a means for measuring the moisture content of the wooden structure, measuring the moisture content of said wooden structure at said depth, and processing the penetration force and moisture measurements to provide information indicative of the strength of the structure.

2. The method of claim 1 wherein each electrode is insulated along its length and uninsulated at its tip and the resistivity of the wooden structure is measured at the tip of each electrode.

3. The method of claim 2 wherein said electrodes are driven into the structure at the base of said structure.

4. Apparatus for diagnosing the strength of an upraised wooden structure having a treated outer layer that includes a body member having locating means for engaging an upraised wooden structure to position the body member along the general longitudinal generatrix of the structure, mounting means for securing the body member to the upraised wooden structure, a pair of parallel spaced apart electrodes movably mounted in said body member and drive means for forcing the electrode tips to a depth of at least approximately 40 mm perpendicularly into said wooden structure to measure the condition of the structure beyond the treated outer layer, means for measuring the force of penetration exerted on said electrodes, means associated with the electrodes for measuring the moisture content of the wooden structure at the depth of penetration, and means for processing the force and moisture content measurements and providing instantaneous information indicative to the strength of the wooden structure.

5. The apparatus of claim 4 wherein said locating means includes two pairs of spaced apart stops arranged symmetrically on either side of the midplane between planes of penetration of said electrodes, said stops being aligned in parallel planes passing through said electrodes.

6. The apparatus of claim 4 wherein each electrode is insulated along its length and the tip of each electrode is uninsulated.

7. The apparatus of claim 4 wherein said means for measuring the moisture content of the wooden structure is arranged to measure the resistivity of the wooden structure at the tip of each electrode.

8. The apparatus of claim 4 that further includes a lever means for driving the electrodes into a wooden structure to said predetermined depth.

\* \* \* \* \*